United States Patent [19]

Klein et al.

[11] 4,136,953

[45] Jan. 30, 1979

[54] NEPHELOMETER WITH DETECTION SYSTEM FOCUSED ON OPTICAL DARK REGION

[75] Inventors: Gerald L. Klein, Orange; Richard C. Meyer, La Habra, both of Calif.

[73] Assignee: Beckman Instruments, Inc., Fullerton, Calif.

[21] Appl. No.: 816,981

[22] Filed: Jul. 19, 1977

[51] Int. Cl.² .................. G01N 21/00; G01N 1/10
[52] U.S. Cl. ............................ 356/339; 356/246; 250/574
[58] Field of Search ............... 356/103, 104, 246; 250/574

[56] References Cited

U.S. PATENT DOCUMENTS 3,758,787  9/1973  Sigrist .......................... 356/104

*Primary Examiner*—Conrad J. Clark
*Attorney, Agent, or Firm*—R. J. Steinmeyer; R. R. Meads; J. R. Shewmaker

[57] ABSTRACT

A nephelometer including an optical excitation system for directing light through a first window area into a cylindrical glass container and an optical detection system for quantitatively monitoring light scattered by a substance within the container and passing therefrom through a second window area. The optical detection system includes a lens system in optical alignment with the second window area and focused on an optical dark region on an inner wall of the container opposite the second window area. The optical dark region is free of internal light reflections. Therefore, the light monitored by the detection system is scattered light from the substance substantially free of internal light reflections representing background error.

9 Claims, 3 Drawing Figures

NEPHELOMETER WITH DETECTION SYSTEM FOCUSED ON OPTICAL DARK REGION

BACKGROUND OF THE INVENTION

1. Field of the Invention

The present invention relates to nephelometers and, more particularly, to a nephelometric detection system for measuring scattered light free of undesired light reflections.

2. Description of the Prior Art

Copending U.S. patent application Ser. No. 796,621, (Anderson et al), assigned to the assignee of the present invention, discloses a system for the nephelometric assay of antigens and antibodies. For this purpose, an antigen-antibody precipitate forming reaction is conducted in an optically transparent sample container or vial, preferably a cylindrical glass vial. An excitation system directs a beam of light into the sample container and a detection system measures light scattered at a forward angle by the precipitate. As set forth in detail in the application, the scattered light signal provides a quantitative measure of the desired antigen or antibody reaction component and additionally provides an indication of which of the two components is present in excess.

In the foregoing nephelometric system, the detection system for viewing light scattered within the sample container includes a light pipe aligned with a window area of the container to intercept light exiting through the window area. While reasonably accurate measurements can be made with such an arrangement, it has been found that a background signal of reflected light is superimposed on the scattered light signal measured by the detection system. The background signal component results from multiple reflections of the excitation beam within the sample container while entering and exiting the container. Since the sample container is cylindrical and formed of glass, it is theorized that the cylindrical air-glass and liquid-glass interfaces produce the undesirable reflections. Whatever the cause of the internal reflections, however, the detection system intercepts many of these reflections thereby superimposing these as a background signal on the desired scattered light signal. As a result the output scatter signal exhibits a relatively low signal-to-background ratio.

In another prior approach, the detection system includes a lens assembly focused at the center of the sample container. While such reduces the background signal to some degree, the background reflections are still intercepted in sufficient quantity to degrade the scattered light signal.

SUMMARY OF THE INVENTION

The present invention resides in a nephelometer which overcomes the disadvantages of prior systems by minimizing the background component of a measured nephelometric signal. The nephelometer comprises an excitation system for directing light from a source through a first window area in a sample container and a detection system for monitoring light scattered by a substance within the container and passed from the container through a second window area. In accordance with a primary aspect of the present invention, an optically dark region of the interior wall of the container opposite the second window area which is free from internal light reflections is isolated for viewing by the detection system. In this regard, the detection system includes means defining a detector window through which light passes to a detector and a lens system optically aligned with the second window area for transferring an image of the isolated dark region on the container wall to the detector window. Slit means in a focal plane of the lens system cooperate with the detector window to limit the rays of light passed to the detector to those between the optically dark region and the second window area. With the detection system thus focused, background light reflections within the sample container are excluded from detection. Consequently, the nephelometer measures the scattered light signal with an increased signal-to-background ratio.

DESCRIPTION OF THE PREFERRED EMBODIMENT

Figure 1:
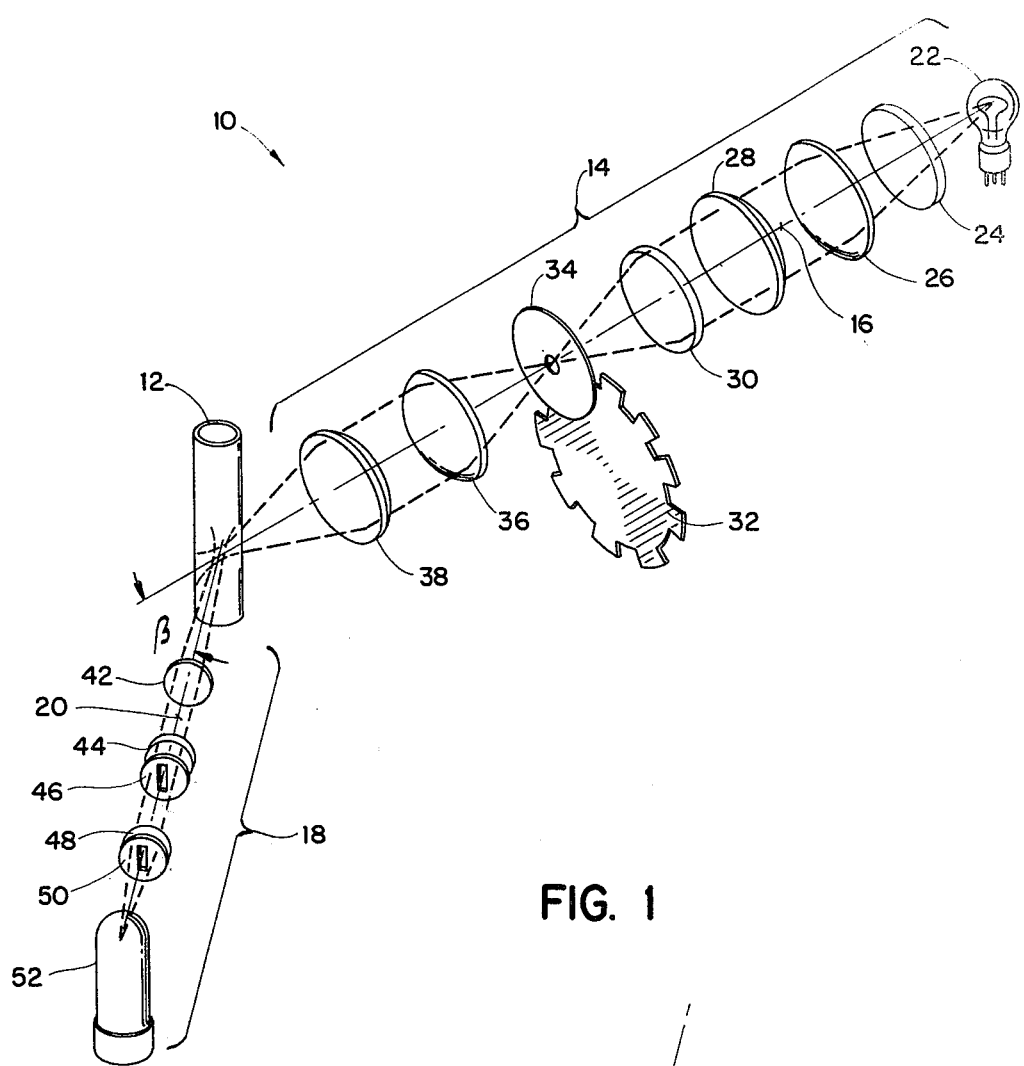
FIG. 1 is a perspective view of the nephelometric optical system of the invention. The figure illustrates a generally vertically disposed sample container, an excitation system for directing light into the container, and a detection system for monitoring light scattered by the container contents at an acute forward angle.

FIG. 1 illustrates the optical arrangement of a nephelometer indicated generally by the numeral 10. The nephelometer includes a sample container 12, preferably an optically transparent, cylindrical glass vial, the interior of which defines a chamber for receiving chemical reactants or other materials to be measured. For the nephelometric assay of antigen and antibody reaction components, the system includes an optical excitation system 14 for directing a beam of light along a predetermined axis 16 into the sample container together with an optical detection system 18 for detecting light scattered by the contents of the container and passing therefrom along an optical axis 20. Axes 16 and 20 lie in a horizontal plane perpendicular to the vertical axis of sample container 12. Optical axis 20 defines an acute forward angle $\beta$ with respect to axis 16.

Excitation system 14 includes a light source 22, a heat absorbing filter 24, a pair of condensing lenses 26 and 28, a second filter 30, an optical chopper 32, a spatial filter 34, and a pair of relay lenses 36 and 38.

Light source 22 preferably comprises an incandescent, tungsten filament lamp the filament of which presents an incandescent surface area approximately 2.5 mm square. Filters 24 and 30 serve to define the bandwidth of spectral energy passed from the source 22 to the sample container 12. For this purpose, filter 24 is formed of heat absorbing glass which attenuates infrared energy above 800 nm. Filter 30 is a thin film glass having pass bands between 400 and 620 nm and between 840 nm and 10 $\beta$. Consequently, the pair of lenses together passes only energy in the range 400–620 nm toward the sample container.

Condensing lenses 26 and 28 together function as a conventional eyepiece to transfer a reduced image of the incandescent lamp filament on the spatial filter 34. The spatial filter is a plate with a small aperture slightly larger than the image of the source filament and functions essentially as a field stop to limit the rays in the excitation system to only those having their origin at the source filament. In this fashion the spatial filter blocks stray radiation and reflections present in the excitation system.

Optical chopper 32, which is positioned in the excitation beam path just ahead of spatial filter 34, is a perforated disc which is rotated for modulating the light beam in a conventional manner.

Relay lenses 36 and 38 function to relay a replica image of the source filament at the spatial filter 34 into the sample container 12. Preferably, the source filament image is placed in the center of the sample container on the vertical axis thereof. It will be appreciated that since sample container 12 is cylindrical, it functions as a lens and such lens action must be compensated for to position the source image at the center of the container. This is accomplished by focusing lens 38 on predetermined axis 16 slightly beyond (i.e. downstream from) the sample container 12. Consequently, when the container is then inserted in place, the source image shifts to the center of the container.

Sample container 12, in the preferred embodiment, comprises a conventional, cylindrical glass shell vial. Shell vials are available in varying heights but having a standard outside diameter of 9.0 mm and a standard wall thickness of 0.5 mm from both the Acme Glass Company and the Brockway Glass Company.

Figure 2:
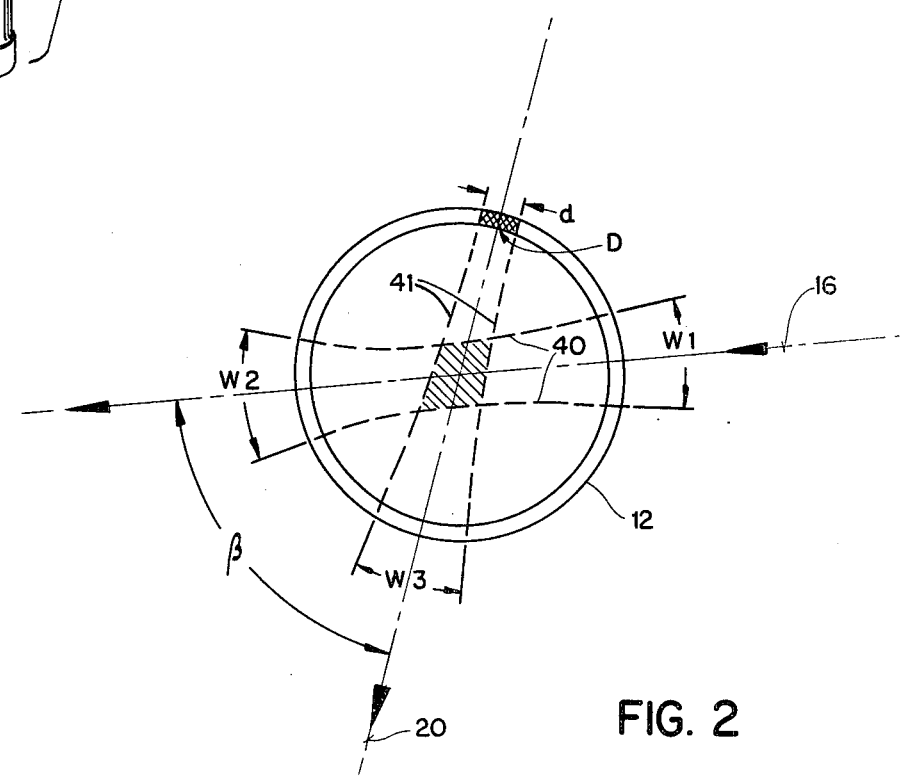
FIG. 2 is an enlarged view, taken in a horizontal plane, through the sample container of FIG. 1 and illustrates the optical axes of the excitation and detection systems and a caustic surface of light across the container.

FIG. 2 illustrates a horizontal section through sample container 12 in the plane of optical axes 16 and 20. The exitation light, which is focused into the center of the sample container by the excitation system 14, enters the container through a window area W1 and exits the container through an opposite window area W2. An illuminated area 40, termed a caustic surface, extends across the container between window areas W1 and W2 as illustrated by a first pair of dashed lines in FIG. 2. The caustic surface is visible when looking down into the container along the vertical axis thereof and, as illustrated, necks down toward the center of the container.

Focusing the exitation energy to place the source image at the center of sample container 12 as described ensures that blur spots at opposite window areas W1 and W2 are essentially equal in size. Any other location of the source would result in one blur spot being larger than the other thereby causing greater internal reflections.

Still with reference to FIG. 2, the optical axis 20 for optical detection system 18 is disposed at the acute forward angle $\beta$, herein between about 60° and 80° and preferably 70°. The scattered light to be measured by the detection system exits the container 12 through a window area W3 on the axis 20. The detection system intercepts an area within the container illustrated by a second pair of dashed lines 41. The area of the caustic surface 40 intercepted by the detection system, and illustrated by hatching, contains the scattered light energy to be monitored by the detection system. Focusing the exitation energy into the center of the container concentrates the luminous flux at the center such that desirable scatter energy for measurement is maximized on detector axis 20.

As noted in the Background, light reflections within the sample container 12 are visible when looking into the container through the scatter measuring window area W3, and these reflections create a background signal which competes unfavorably with the scattered light signal to be measured. Applicants have not determined the specific cause of such reflections. In any case, when the sample container is empty, the reflections are readily observed in the foregoing optical system in the form vertically (axially) extending, circumferentially spaced bright bands on the interior wall of the container.

Applicants have also observed that at least one vertically extending contrasting optical dark band or region D is present on the wall of the sample container opposite the scatter window area W3. The dark band is free of internal light reflections. In FIG. 2 the dark band is illustrated by the cross hatching of the container wall. The width "d" of the dark band has been found to be approximately one millimeter in the horizontal plane of FIG. 2.

Figure 3:
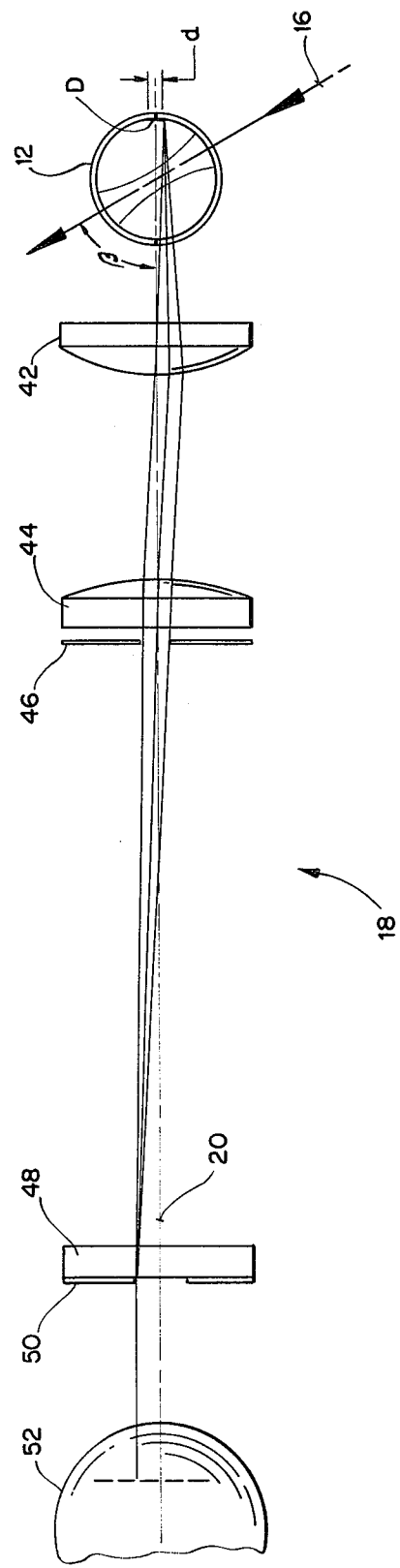
FIG. 3 is an optical diagram of the detection system of FIG. 1.

Applicants have discovered that focusing the detection system 18 on the wall of the sample container 12 opposite the scatter window area W3, and specifically on an optical dark band D thereat, essentially precludes the measurement of internally reflected light and hence eliminates the undesirable background signal introduced by such reflections. To this end, referring now to FIG. 3, the optical detection system 18 includes a pair of lenses 42 and 44, a back focal plane mask 46, a secondary filter 48, a field stop 50, and an optical detector 52.

Secondary filter 48 is a 560 nm cut-off filter for defining a pass band of wavelengths between 400 and 560 nm for transmission to detector 52. Detector 52 is preferably a photomultiplier tube, the active area of which has been illustrated by a dashed line in FIG. 3.

Field stop 50 comprises a slit located in the image plane of the optical detection system 18 in front of detector 52. Lenses 42 and 44, of the plano-convex type, are focused on the optical dark region D on the interior wall of sample container 12 opposite the scatter window area W3. The relative positions of the lenses and the field stop along the optical axis 20 is such that with the lenses focused as described, they function as an eyepiece to transfer a magnified image of the optically dark region D onto the field stop 50. The slit width of the field stop is the same as the magnified image of the optical dark region. In this manner, the field stop functions to define a detector window through which light passes along optical axis 20 to the detector 52. In the preferred embodiment, for a 1 mm. diameter dark region D and 3X magnification by lenses 42 and 44, the field stop slit width is approximately 3 mm.

Mask 46 is positioned on optical axis 20 in the back focal plane of lens assembly 42-44 between the lenses and the field stop 50. The back focal plane mask forms an aperture stop for eliminating stray light in the detection system by rejecting light having an origin outside of dark region D within the container 12. In the disclosed embodiment, the slit width of mask 46 is about 2 mm.

In operation, lenses 42 and 44, mask 46, a field stop 50 together function as a telescope which limits the rays of light passed to the photomultiplier 52 to only those which originate from the optical dark band D on the sample container wall and the generally conical area between the dark band and lens 42. Consequently, internal reflections within the container, visible as bright bands around the container wall, are not intercepted by the detection system. In this manner a scattered light signal is derived exhibiting a signal-to-background ratio as much as two hundred times greater than prior systems.

While the nature and type of optical components in the foregoing system will vary depending upon the type of scattering measurements to be made, one successfully operated system employed the following specific components. The distance of each component along appropriate one of axes 16 or 20 measured from the vertical axis of sample container 12, is indicated parenthetically for each component:

OPTICAL EXCITATION SYSTEM 14

Light source 22 (215.9 mm)
Heat absorbent filter 24 (185 mm approx.)
Condensing lens 26 (150.5 mm) — 50 mm focal length
Condensing lens 28 (129.2 mm) — 38 mm focal length
Second filter 30 (120 mm approx.)
Optical chopper 32 (105 mm approx.)
Spatial filter 34 (100.0 mm)
Relay lens 36 (63.8 mm) — 38 mm focal length
Relay lens 38 (32.0 mm) — 38 mm focal length
Sample container 12 (000.0 mm)

OPTICAL DETECTION SYSTEM 18

Detector 52 (84.0 mm approx.)
Field Stop 50 (74.2 mm)
Secondary filter 48 (70 mm approx.)
Back focal plane mask 46 (31.5 mm)
Lens 44 (30.0 mm) — 31 mm focal length
Lens 42 (10.0 mm) — 24 mm focal length While a preferred embodiment of the invention has been illustrated and described, it will be apparent that modifications may be made therein without departing from the invention defined in the appended claims.

What is claimed is:

1. A nephelometer comprising:
a source of light;
a container including in a wall thereof a first window area for passing light from the source in a forward direction into the container to impinge upon a substance therein and to scatter therefrom, and a second window area for passing from the container a portion of the light scattering in a forward direction from the substance;
a first lens system having an optical axis passing through the second window area and an area in the container where light from the source impinges upon and scatters in a forward direction from the sample, and focused on an optical dark region on an inner wall of the container opposite the second window area; and
a light detector for monitoring light passing from the container and through the first lens system along the optical axis.

2. The nephelometer of claim 1 further including:
a second lens system for directing light from the source in the forward direction and along a predetermined axis through the first window area to a predetermined area within the container; and
wherein the optical axis of the first lens system passes through the predetermined area and intersects the predetermined axis at an acute forward angle relative to the predetermined axis.

3. The nephelometer of claim 2 wherein:
the container is of substantially circular cross section in a plane including the optical and predetermined axes; and
the second window area in the container is circumferentially spaced from the first window area by an angle greater than 90° and less than 180°.

4. The nephelometer of claim 3 wherein the optical axis and the predetermined axis define a forward acute angle of between about 60° and 80°.

5. The nephelometer of claim 3 wherein:
said second lens system transfers an image of the light source into the center of said container.

6. The nephelometer of claim 3 further including:
means defining a detector window on said optical axis through which light is passed to said detector, the relative positions of said detector window and said first lens system being such that said first lens system transfers an image of said optical dark region into said detector window.

7. The nephelometer of claim 6 further including:
slit means on said optical axis in a focal plane of said first lens system between said first lens system and said detector window defining an aperture stop for limiting light rays passed to said detector window to those between said optical dark region and said second window area.

8. The nephelometer of claim 1 further including:
means defining a detector window on said optical axis through which light is passed to said detector, the relative positions of said detector window and said first lens system being such that said first lens system transfers an image of said optical dark region into said detector window.

9. The nephelometer of claim 8 further including:
slit means on said optical axis in a focal plane of said first lens system between said first lens system and said detector window defining an aperture stop for limiting light rays passed to said detector window to those between said optical dark region and said second window area.

* * * * *